(12) United States Patent
Chou et al.

(10) Patent No.: US 11,696,723 B2
(45) Date of Patent: Jul. 11, 2023

(54) DEVICES, SYSTEMS, AND METHODS FOR MONITORING HAIR

(71) Applicant: Essenlix Corporation, Monmouth Junction, NJ (US)

(72) Inventors: Stephen Y. Chou, Princeton, NJ (US); Wei Ding, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/975,752

(22) Filed: Oct. 28, 2022

(65) Prior Publication Data

US 2023/0061137 A1 Mar. 2, 2023

Related U.S. Application Data

(63) Continuation of application No. 16/772,852, filed as application No. PCT/US2018/065865 on Dec. 14, 2018, now Pat. No. 11,510,608.

(60) Provisional application No. 62/598,750, filed on Dec. 14, 2017.

(51) Int. Cl.
G16H 30/20 (2018.01)
G01N 33/53 (2006.01)
A61B 5/00 (2006.01)
G16H 50/20 (2018.01)
G06T 7/00 (2017.01)

(52) U.S. Cl.
CPC ............ *A61B 5/448* (2013.01); *G01N 33/53* (2013.01); *G06T 7/0012* (2013.01); *G16H 30/20* (2018.01); *G16H 50/20* (2018.01); *G06T 2207/30004* (2013.01)

(58) Field of Classification Search
CPC .......... A61B 5/448; G16H 5/02; G01N 33/53; G06T 7/0012; G06T 2207/300044
See application file for complete search history.

(56) References Cited

U.S. PATENT DOCUMENTS

| | | |
|---|---|---|
| 3,368,872 A | 2/1968 | Natelson |
| 3,436,140 A | 4/1969 | Lord |
| 3,447,863 A | 6/1969 | Patterson |
| 3,554,631 A | 1/1971 | Beyer et al. |
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |

(Continued)

FOREIGN PATENT DOCUMENTS

| | | |
|---|---|---|
| AU | 198813789 A | 9/1988 |
| AU | 619459 B | 1/1992 |

(Continued)

OTHER PUBLICATIONS

Written Opinion for PCT/US18/65865 established by ISA/US dated Jun. 19, 2019.

*Primary Examiner* — David P Porta
*Assistant Examiner* — Fani Polyzos Boosalis

(57) ABSTRACT

Device, systems, and methods are provided that can be used to monitor, examine, and/or analyze hair conditions and make suggestions to improve the hair conditions.

35 Claims, 7 Drawing Sheets

(56) References Cited

U.S. PATENT DOCUMENTS

| | | |
|---|---|---|
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2003/0215810 A1 | 11/2003 | Lu et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |

(56) References Cited

U.S. PATENT DOCUMENTS

| | | |
|---|---|---|
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0269436 A1* | 10/2012 | Mensink .............. G06V 20/00 382/180 |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0182318 A1 | 7/2013 | Eastman et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2013/0315465 A1* | 11/2013 | Cosatto ................ G06T 7/0012 382/133 |
| 2014/0154789 A1* | 6/2014 | Polwart .............. G01N 21/8483 422/403 |
| 2014/0315242 A1 | 10/2014 | Rodriguez et al. |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 | 6/2001 |
| CN | 1302229 | 7/2001 |
| CN | 1166950 | 9/2004 |
| CN | 1188217 | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2002023154 A2 | 3/2002 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017048871 | 3/2017 |
| WO | 2017048871 A1 | 3/2017 |
| WO | 2019027963 A1 | 2/2019 |

* cited by examiner

QMAX plate with and without a groove
Fig. 1A Two plates at an open configuration
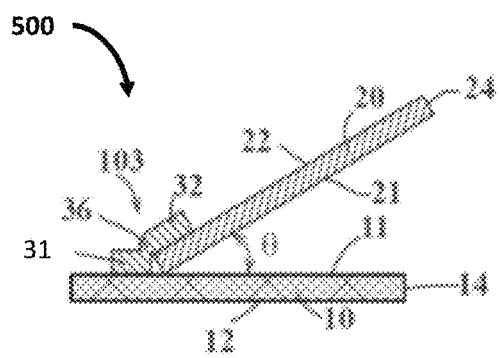
Two plates at a closed configuration
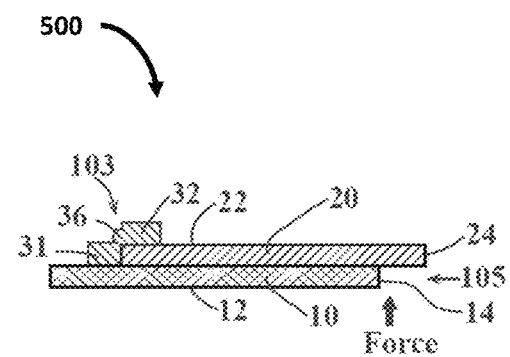
Fig. 1B
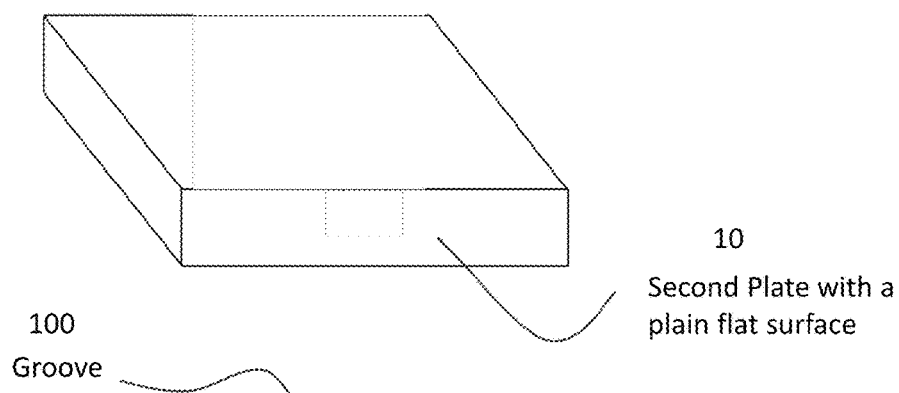
10 Second Plate with a plain flat surface
100 Groove
Fig. 1C
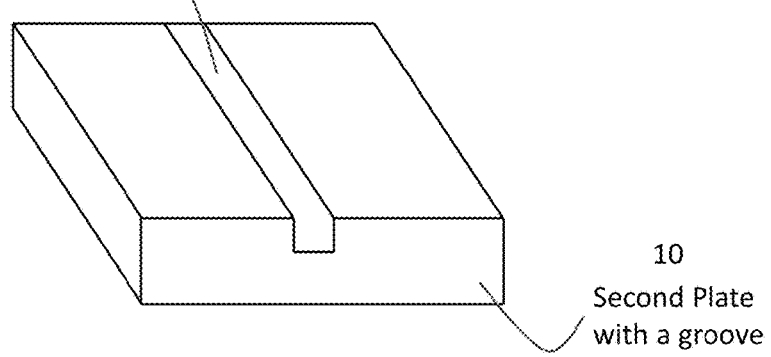
10 Second Plate with a groove Viewing from the angle across the groove Viewing from the angle along the groove Viewing from the angle along the groove QMAX plate with a groove and lateral hand motion of rubbing strands of hair into groove QMAX plate with strands of hair in groove after lateral hand motion

DEVICES, SYSTEMS, AND METHODS FOR MONITORING HAIR

CROSS-REFERENCING

This application is a continuation of U.S. non-provisional application Ser. No. 16/772,852, filed on Jun. 15, 2020, which is a National Stage entry (§ 371) application of International Application No. PCT/US18/65865, filed on Dec. 14, 2018, which claims the benefit of U.S. Provisional Patent Application No. 62/598,750, filed on Dec. 14, 2017, the contents of which are relied upon and incorporated herein by reference in their entirety.

The entire disclosure of any publication or patent document mentioned herein is entirely incorporated by reference.

FIELD OF THE INVENTION

The present invention provides, among other things, devices, systems, and methods for monitoring and analyzing hair conditions.

BACKGROUND OF THE INVENTION

Hair is not only important for aesthetic appeal of a person, but also reflects his/her health condition and/or living habits. The present invention relates to devices, systems, and methods that can be used to monitor, examine, and/or analyze hair conditions and make suggestions to improve the conditions.

BRIEF DESCRIPTION OF THE DRAWINGS

The skilled artisan will understand that the drawings, described below, are for illustration purposes only. The Figures do not intend to show the elements in strict proportion. For clarity purposes, some elements are enlarged when illustrated in the Figures. The dimensions of the elements in the Figure should be delineated from the descriptions herein provided and incorporated by reference. The drawings are not intended to limit the scope of the present teachings in any way. In some Figures, the drawings are not in scale. In the figures that present experimental data, the lines that connect data points are for viewing the data only and do not have other means.

FIGS. 1A-C provide schematic illustrations of some embodiments of a device for handling and monitoring hairs. A hair holder comprising a first plate and a second plate. In some embodiments, the inner surface (i.e. the surface in contact with hair sample) are flat. In some embodiments, one of the plate has one or a plurality of grooves for restricting the movement hairs for the location of the grooves.

DETAILED DESCRIPTION OF EXEMPLARY EMBODIMENTS

Figure 2A:
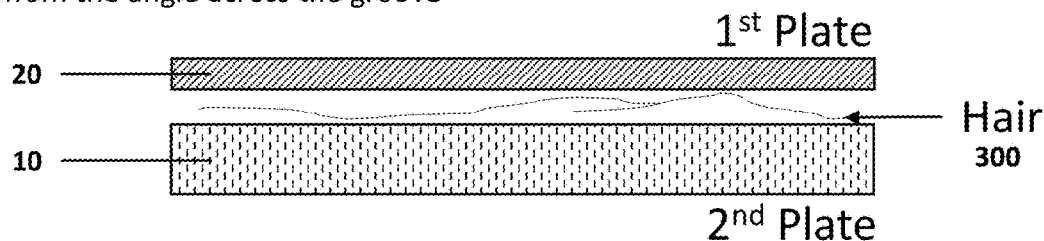
FIG. 2A provides a schematic illustration showing an embodiment of the present invention. A hair holder comprising a first plate and a second plate, wherein the plates accommodate a plurality of hairs and restrict the movement hairs.

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

1. Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The term "monitoring" and "examining" and "analyzing" are interchangeable.

The term "subject" refers to any animal or person. In some embodiments, the term "subject" is a mammal that has hair.

The terms "hair" and "hairs" refer to any filament that is man-made or grow from the skin of an animal or a person or otherwise derived from an animal or a person. While "hair" refers to a single hair filament or a collection of all hairs from a subject, "hairs" refers to a plurality of hair filaments.

The term "hair status" refers to one or more traits including but not limited to hair density, hair color, hair smoothness, hair texture, hair thickness, hair curliness, and hair volume.

The term "imager" refers to a device or component of a device that includes optical parts and is configured to capture images of a sample (e.g., hairs). In some embodiments, the imager is camera. In certain embodiments, the imager is a camera that is part of a smart phone.

The term "detector" refers to devices that are configured to detect and/or measure signals gathered by the detector and/or other devices/components. In some embodiments, the detector refers to a mobile device. In certain embodiments, the detector is a smart phone.

The term "mobile device" refers to a detector that is a computing device small enough to hold and operate in the hand. Mobile device includes, but is not limited to: mobile internet devices, tablet computers, laptops, wearable computers, calculator watches, smartwatches, head-mounted displays, personal digital assistants, enterprise digital assistants, calculators, handheld game consoles, portable media players, ultra-mobile PCs, digital media player, digital still cameras (DSC), digital video cameras (DVC) or digital camcorders, mobile phones, smartphone, feature phones, pagers, personal navigation devices (PND), smart cards, or project Ara.

The term "software" refers to a series of instructions that are configured to direct, manipulate, and/or cause a processor (e.g. a central processing unit) and associated hardware to perform specific functions, calculations, and/or operations. In some embodiments, the software is stored in and used by a computing device.

The terms "monitoring", "examining" and "analyzing" are interchangeable.

It will be understood that embodiments of the present disclosure are not limited to analyzing hair (e.g., the sample can be hair). In certain embodiments, the sample can be a natural material (e.g., hair), a synthetic material (e.g., nylon), or a naturally occurring material that is synthetically modified. The sample can be selected from the group consisting of hair, a glass fiber, a glass microfiber, a cellulose fiber, a nitrocellulose fiber, a cellulose acetate fiber, a nylon fiber, a polyolefin fiber, a polyester fiber, a polycarbonate fiber, a polypropylene fiber, a polyvinylidene difluoride fiber, a polyethylene fiber, a polystyrene fiber, a polyurethane fiber, a polyphenylene oxide fiber, a poly(tetrafluoroethylene-co-hexafluoropropylene) fiber, a quartz fiber, a hydrophilic polymer/fiber, fiberglass, silk, spider silk, seed fiber, leaf fiber, bast fiber, fruit fiber, stalk fiber, animal fibers (e.g., collagen, keratin, fibroin, wool, cashmere, camel hair, or avian fibers), chitin, chitosan, cotton, flax, hemp, jute, natural fiber composites, and any combination thereof. Hydrophilic polymers/fibers can be polyester fibers, polyamide fibers or carbohydrate polymer fibers.

In certain embodiments of the present disclosure, the cross-sectional diameter of a sample (e.g., a natural fiber or a synthetic fiber) can be less than about 1000 microns ($\mu$m or $\mu$m), less than about 750 $\mu$m, less than about 500 $\mu$m, less than about 400 $\mu$m, less than about 300 $\mu$m, less than about 200 $\mu$m, less than about 175 $\mu$m, less than about 150 $\mu$m, less than about 125 $\mu$m, less than about 100 $\mu$m, less than about 90 $\mu$m, less than about 80 $\mu$m, less than about 70 $\mu$m, less than about 60 $\mu$m, less than about 50 $\mu$m, less than about 40 $\mu$m, less than about 30 $\mu$m, less than about 20 $\mu$m, less than about 10 $\mu$m, or less than about 5 $\mu$m. In certain embodiments, the cross-sectional diameter of a sample (e.g., a natural fiber or a synthetic fiber) can be a range between two values. For example, the cross-sectional diameter of a sample (e.g., a natural fiber or a synthetic fiber) can be between about 5 $\mu$m and 500 $\mu$m. In another example, the cross-sectional diameter of a sample (e.g., a natural fiber or a synthetic fiber) can be between about 10 $\mu$m and 250 $\mu$m. In yet another example, the cross-sectional diameter of a sample (e.g., a natural fiber or a synthetic fiber) can be between about 15 $\mu$m and 200 $\mu$m.

2. Working Principle

It is often desirable to monitor (including analyze) the hair status of the hair of an animal or a person. In addition, when monitoring hair status, it is desirable to place the hair in a restricted space so that imaging and/or processing of signals can be conducted reliably. In some embodiments, the present invention provides devices, systems, and methods that can be used to restrict the movement of hairs and facilitate monitoring hair status.

A. Hair Monitoring Device

In some embodiments, the present invention discloses an apparatus for monitoring hair status of a subject, the apparatus includes:

(a) a hair holder that is configured to accommodate a plurality of hairs and restrict the movement of the hairs, wherein the hair holder comprises a liquid material that is in contact with the hairs, and (b) an adaptor that is configured to connect the hair holder to a mobile device, wherein, when attached to the mobile device, the adaptor positions the hairs in the hair holder in a field of view of an imager, which is a part of or an entirety of the mobile device, wherein the imager is configured to capture images of the hairs and the mobile device is configured to analyze, or digitally transmit images of the hairs or processed results of the images of the hairs to a remote third party for further analysis.

B. Hair Monitoring Process

In some embodiments, the present invention discloses a process for monitoring hair status of a subject, the process includes:

(a) obtaining a hair holder that is configured to accommodate a plurality of hairs and restrict movement of the hairs;

(b) obtaining an adaptor that is configured to accommodate the hair holder and be attachable to a mobile device;

(c) placing hairs in the hair holder and inserting the hair holder into the adaptor, wherein the hair holder comprises a liquid material that is in contact with the hairs, (d) attaching the adaptor to the mobile device;

(e) capturing images of the hair in the hair holder with an imager, wherein the imager is a part of or the entirety of the mobile device; and (f) analyze, or digitally transmit images of the hairs or processed results of the images of the hairs to a remote third party for further analysis.

According to the present invention, the hair monitoring also include, but not limited, to the chemical and biological analysis of a hair. The chemical analysis of the hair include, but not limited, to measuring the hair's PH value, and reactions with chemical reagents. The biological analysis include analysis of proteins, nuclear acids, small molecules, cells, bacterial, virus, and others in or on a hair. The chem/bio analysis are further disclosed in the rest of the disclosure.

3. Exemplary Embodiments

FIG. 1 provides schematic illustrations of some embodiments of a device for handling and monitoring hairs. A hair holder comprising a first plate 20 and a second plate 10. In some embodiments, the inner surface (i.e., the surface in contact with hair sample) of second plate 10 is flat. In some embodiments, one of the plates (e.g., second plate 10) has one or a plurality of grooves (100) for restricting the movement hairs for the location of the grooves.

The first plate 20 and the second plate 10 are movable relative to each other into different configurations, including an open configuration, and a closed configuration. The open configuration is a configuration that the two plates are a part and the hairs are deposited on one or both plates. In the closed configuration, the two plates (i) work together to restrict the deposited hair, or (ii) are in direct touch.

In some embodiments, there is a hinge 103 to connect the first plate 20 and the second plate 10, so that they rotate from each other about the hinge 103.

In some embodiments, one or both of the plates comprises spacers (not shown in FIG. 1). More specification of the spacers is given in the other part of the disclosure.

FIG. 1A, FIG. 1B, and FIG. 1C provide schematic illustrations of several embodiments of the present invention. In some embodiments, a hair holder 500 comprises a first plate 20 and a second plate 10, wherein the plates accommodate a plurality of hairs. In some additional embodiments, the hair holder 500 comprises a first plate 20 and a second plate 10 with a groove 100, wherein the second plate 10 with the groove 100 (located on the inner surface) can accommodate at least one strand of hair and restrict the movement of the at least one strand of hair. In some embodiments, the hair holder 500 comprises a liquid material that is configured to restrict the movement of the hairs. In some embodiments, the liquid material can solidify after a period of time and hold the hair in place for detection and measurement.

Figure 2B:
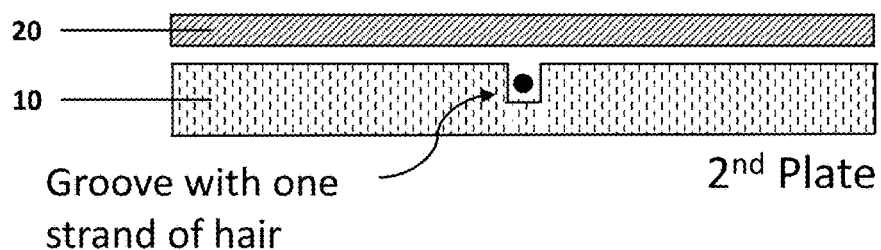
FIG. 2B provides a schematic illustration showing an embodiment of the present invention. A hair holder comprising a first plate and a second plate with a groove, wherein the plates can accommodate at least one strand of hair and restrict the movement of the one strand of hair.
Figure 2C:
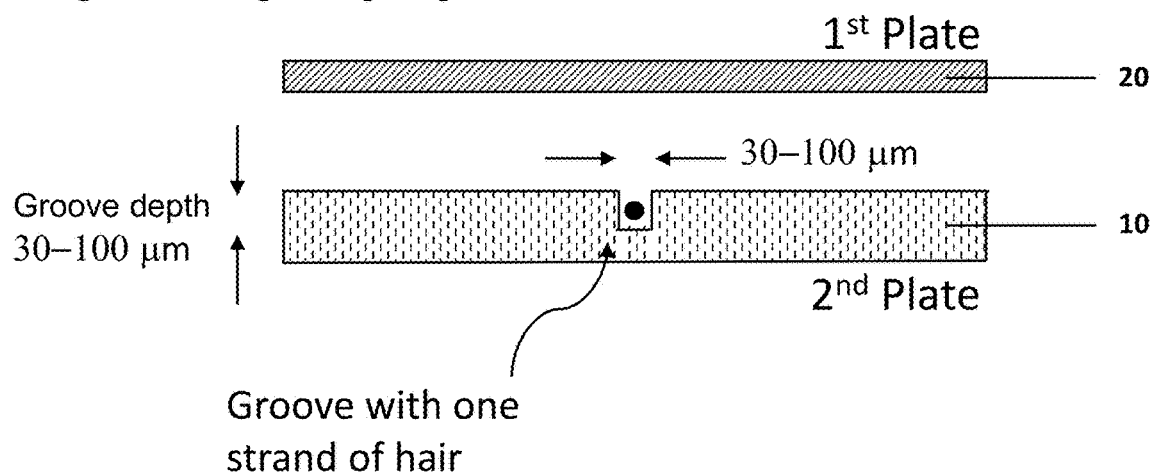
FIG. 2C provides a schematic illustration showing a preferred embodiment of the present invention wherein the hair holder comprises a second plate with a groove that has the preferred dimensions of range of 30 μm to 100 μm, which can accommodate one strand of hair.

FIG. 2 provides a schematic illustration showing an embodiment of a device and a method to fix at least a strand of hair into a fixed location of a sample card. A sample card comprises a first plate 20 and a second plate 10, wherein a groove 100 on an inner surface of one of the plates. Hair is deposited on the surface of a plate but outside the groove 100 first, then use hand to rub the deposited hair of the plate surface back and forth cross the groove, so that the rubbing makes some of the hairs logged into the groove 100. One reason to put a hair into a groove is to fix the hair into a specific location of the plate, so that the hair can be easily observed when the plate is inserted into a reader.

In some instances, the at least one strand of hair 300 is placed in the groove of the second plate 10 by rubbing a plurality of hairs by hand to position the at least one strand of hair in the groove.

A groove 100 has a width, a length and a depth. The width and the length are in the plane that is the same as the sample plate surface, while the groove depth is normal to the plate surface.

In some embodiments, the groove depth is 0.1 µm, 1 µm, 10 µm, 30 µm, 40 µm, 50 µm, 60 µm, 70 µm, 80 µm, 90 µm, 100 µm, 110 µm, 120 µm, 130 µm, 200 µm, 300 µm, 400 µm, 500 µm, 1 mm, 2 mm, or a range between any of these values.

In some embodiments, the groove width is 1 µm, 10 µm, 30 µm, 40 µm, 50 µm, 60 µm, 70 µm, 80 µm, 90 µm, 100 µm, 110 µm, 120 µm, 130 µm, 200 µm, 300 µm, 400 µm, 500 µm, 1 mm, 2 mm, 3 mm, 5 mm, 8 mm, or a range between any of these values.

In some embodiments, the groove length is 100 µm, 110 µm, 120 µm, 130 µm, 200 µm, 300 µm, 400 µm, 500 µm, 1 mm, 10 mm, 20 mm, 50 mm, 80 mm, or a range between any of these values. In some embodiments, the groove crosses the width of the plate as shown in FIG. 2 (so the groove length is the same as the width of the plate) In some embodiments, the groove crosses the length of the plate.

In some embodiments, the groove cross-section is round, ellipse, square, rectangle, triangle, polygon, ring-shaped, any superposition of these shapes, or any shape that accommodating hair strand. In some embodiments, the groove cross-section is rectangle, half-circle, or ellipse.

In some embodiments, the dimensions of the groove are selected to accommodate one strand of hair, so that the location of the hair is on or near the groove 100.

Figure 3:
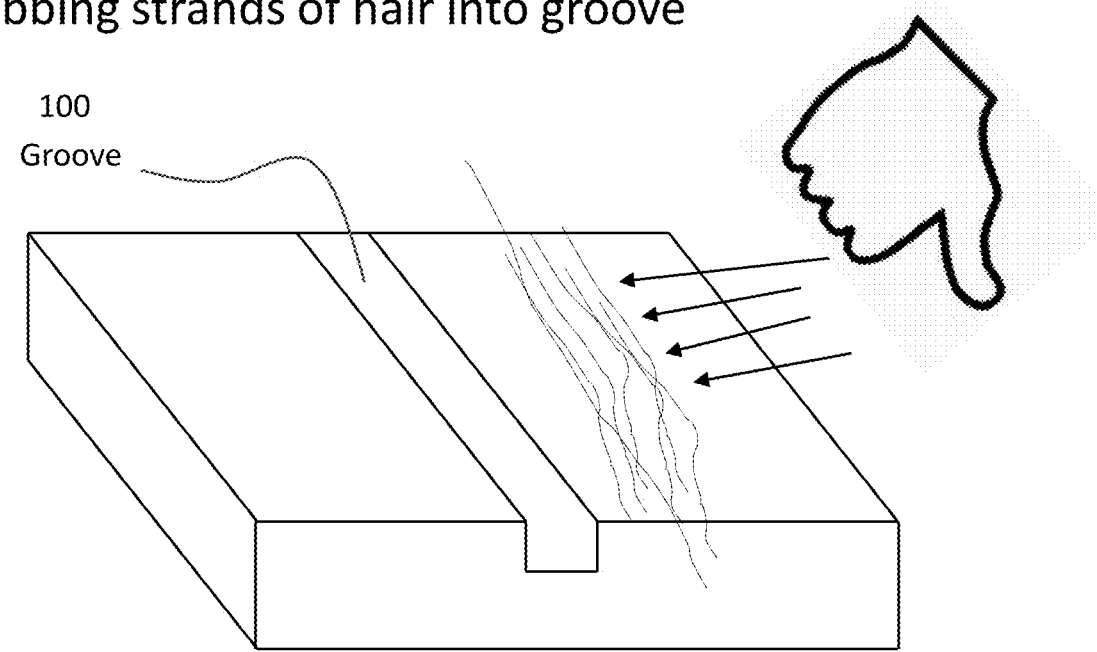
FIG. 3 provides a schematic illustration showing an embodiment of a device and a method to make at least a strand of hair into a fixed location of a sample card by hand, and the location is defined by a groove.
Figure 3:
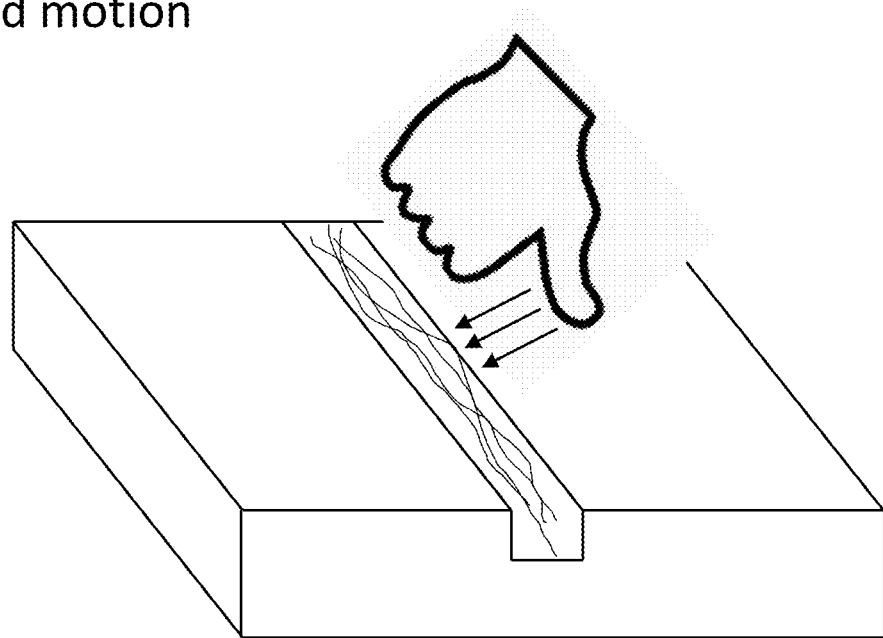

FIG. 3 provides a schematic illustration showing lateral hand motion of before and after rubbing strands of hair into the groove.

Figure 4:
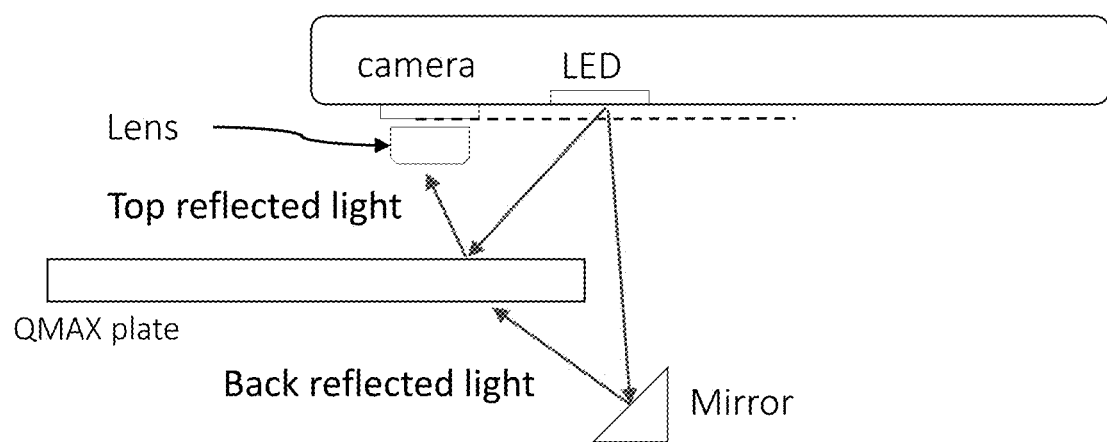
FIG. 4 provides a schematic illustration showing an optical design for an embodiment of the present invention, wherein the hair holder can be used together with an adaptor comprising optical components.

FIG. 4 provides a schematic illustration showing an optical design for an embodiment of the present invention, wherein the hair holder can be used together with an adaptor that comprises various optical components. In some embodiments, the mobile device comprises an imager (camera) and an illumination source (LED). In some embodiments, the mobile device can be a smartphone. In some embodiments, the sample is a QMAX device is disclosed and described below. In some embodiments, the sample is illuminated by front illumination (light reflected from the sample to the camera) only. In some embodiments, the sample illuminated by back illumination (light going through the sample to reach the camera) only. In some embodiments, the sample is illuminated by both front illumination and back illumination. In certain embodiments, the back illumination is provided by a mirror.

Figure 5:
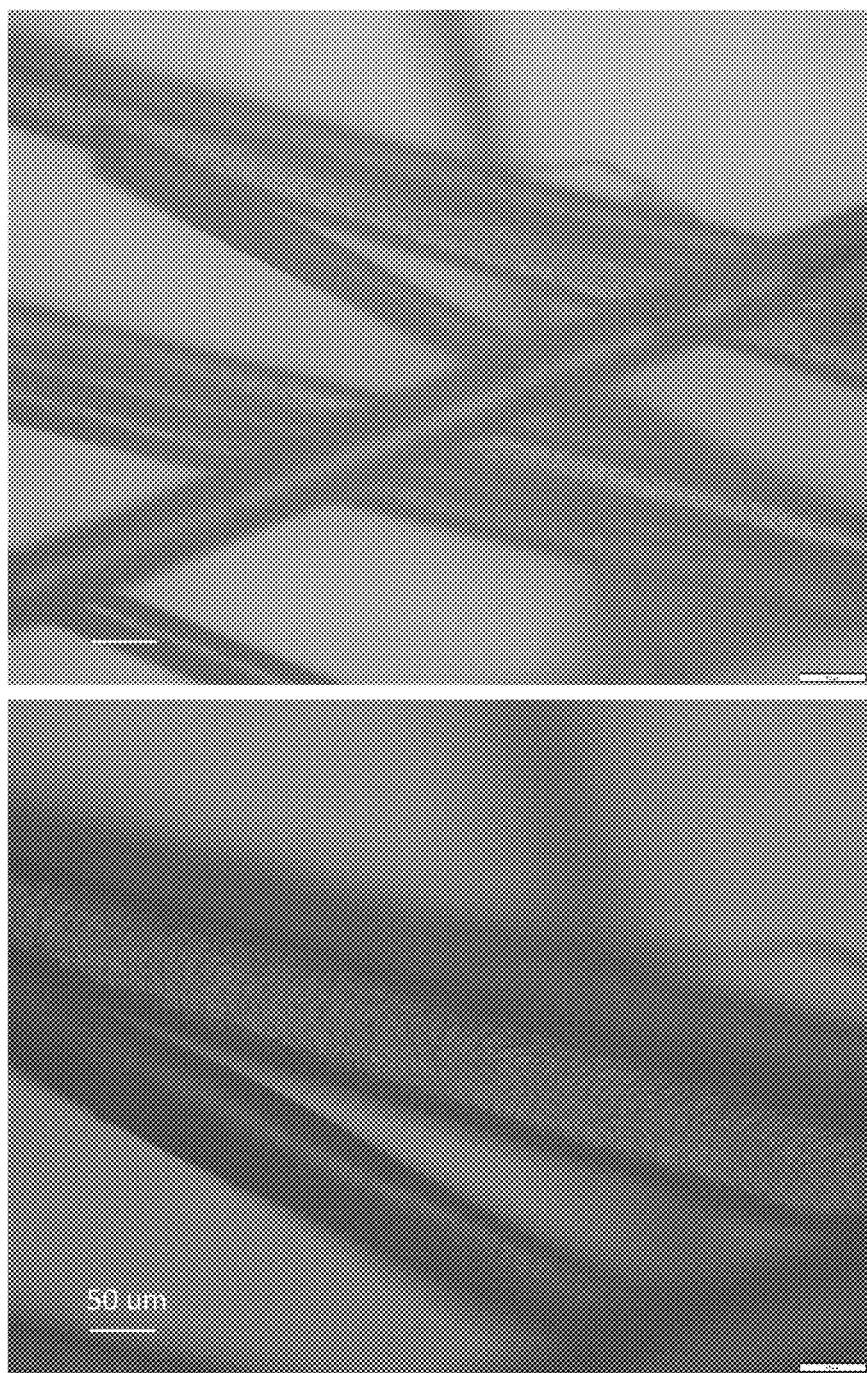
FIG. 5 provides exemplary images of hairs in the hair holder, demonstrating bright-field microscopy images of hairs sandwiched between two plates.

FIG. 5 shows exemplary images of the hairs in the hair holder, demonstrating bright-field microscopy images of the hairs sandwiched between two plates. For the exemplary embodiment shown in this figure, the first plate is 175 µm thick PMMA and the second plate 1 mm thick PMMA. The pictures were taken with a microscope.

Figure 6:
FIG. 6. provides exemplary images of hairs in the hair holder, demonstrating bright-field images of hairs taken by a camera in a smart phone.
Figure 6:
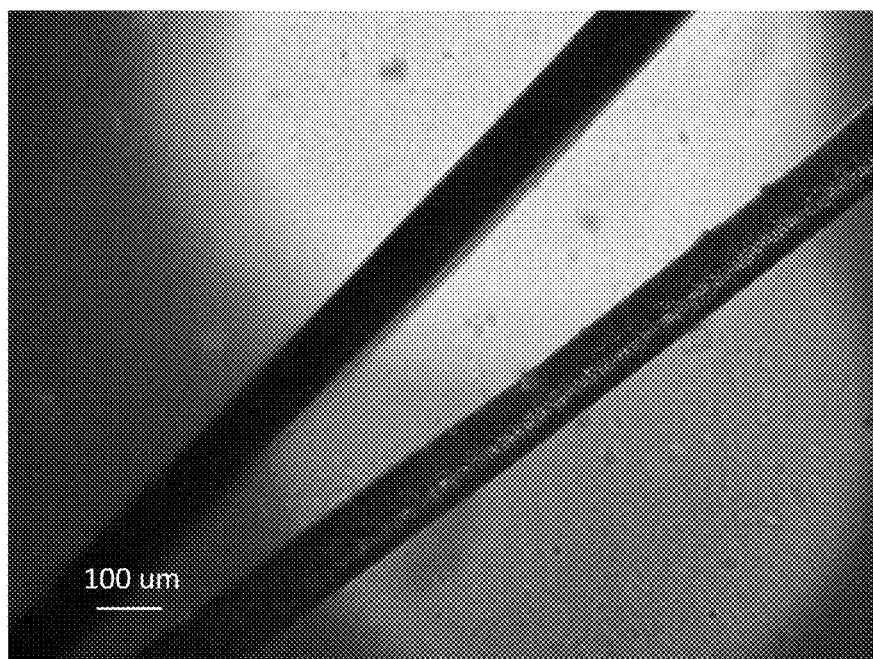

FIG. 6 shows exemplary images of the hairs in the hair holder, demonstrating bright-field images of the hairs taken by a camera in a smart phone. For the exemplary embodiment shown in this figure, the first plate is 175 µm thick PMMA and the second plate 1 mm thick PMMA. The lens used before iphone 7® plus camera has a focal distance of 4 mm.

Figure 7:
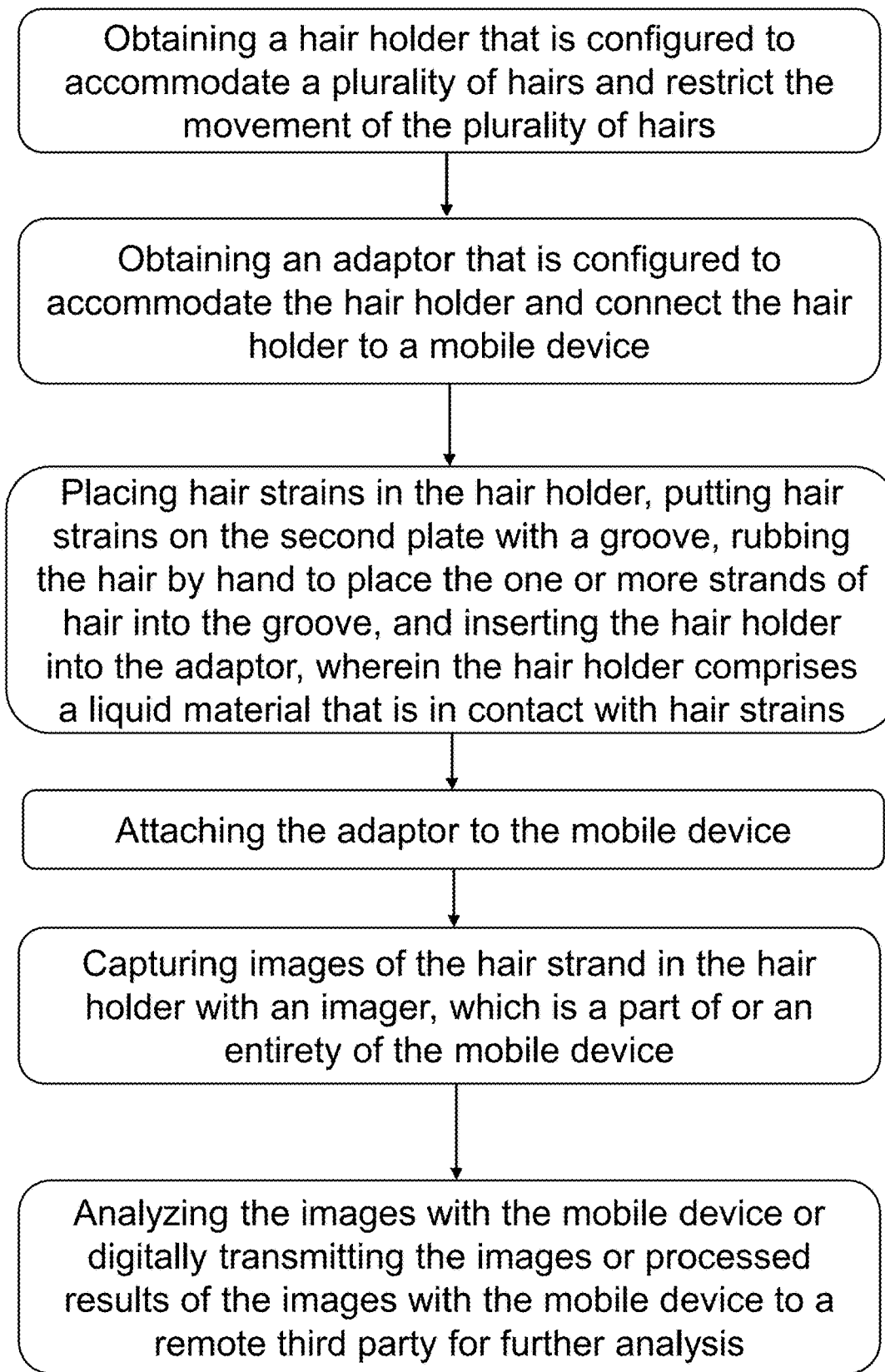
FIG. 7. provides an exemplary flow chart that demonstrates the process to monitor hairs from a subject.

FIG. 7 shows an exemplary flow chart that demonstrates the process to monitor the hairs from a subject. In some embodiments, the process of monitor the hairs includes:

(a) obtaining a hair holder that is configured to accommodate a plurality of hairs and restrict the movement of the hairs;

(b) obtaining an adaptor that is configured to connect the hair holder to a mobile device;

(c) placing hairs in the hair holder and inserting the hair holder into the adaptor, wherein the hair holder comprises a liquid material that is in contact with the hairs, (d) attaching the adaptor to the mobile device;

(e) capturing images of the hair in the hair holder with an imager, which is a part of or an entirety of the mobile device; and (f) analyzing the images with the mobile device or digitally transmitting the images or processed results of the images with the mobile device to a remote third party for further analysis.

4. Hair Holder

In certain embodiments, the hair holder is a QMAX device (or CROF device) as described in PCT/US16/51775 filed on Sep. 14, 2016, which is incorporated by reference by its entirety for all purposes.

In some embodiments, the hair holder comprises a QMAX card (Q-card), which comprises a first plate, a second plate, and spacers, wherein the spacers are configured to regulate a gap between the plates when the plates are pressed against each, compressing the hairs and restrict the movement of the hairs. In certain embodiments, the first plate and the second plate of the Q-card are connected by a hinge, which allows the two plates to pivot against each other.

5. Liquid to Restrict Hairs

In some embodiments, a liquid can be used to restrict the movement of the hairs in a hair holder. In some embodiments, a liquid can be used to restrict the movement of the hairs in a hair holder with a groove in one of the plates of the hair holder. In some embodiments, the liquid is a non-adhesive material such as but not limited to water, ethanol, and oil. In some embodiments, the liquid is an adhesive material (glue). The term "glue" as used herein, means any adhesive substance used for sticking objects or materials together. In some embodiments, the adhesive material the glue is made from include, but not limited to: starch, dextrin, gelatin, asphalt, bitumin, polyisoprenenatural rubber, resin, shellac, cellulose and its derivatives, vinyl derivatives, acrylic derivatives, reactive acrylic bases, polychloroprene, styrene-butadiene, sytyrene-diene-styrene, polyisobutylene, acrylonitrile-butadiene, polyurethane, polysulfide, silicone, aldehyde condensation resins, epoxide resins, amine base resins, polyester resins, polyolefin polymers, soluble silicates, phosphate cements, or any other adhesive material, or any combination thereof. In some embodiments, the glue is drying adhesive, pressure-sensitive adhesive, contact adhesive, hot adhesive, or one-part or multi-part reactive adhesive, or any combination thereof. In some embodiments, the glue is natural adhesive or synthetic adhesive, or from any other origin, or any combination thereof. In some embodiments, the glue is spontaneous-cured, heat-cured, UV-cured, or cured by any other treatment, or any combination thereof.

6. Bio and Chemical Analysis of Hair

According to the present invention, the hair monitoring also include, but not limited to, the chemical and biological analysis of a hair. The chemical analysis of the hair include, but not limited to, measuring the hair's PH value, and reactions with chemical reagents. The biological analysis include analysis of proteins, nuclear acids, small molecules, cells, bacterial, virus, and others in or on a hair. The assays used for analyzing hair include, but not limited to, immunoassay, nucleic assay, colorimetric assay, immunocytochemistry, and spectroanalyzers. The chem/bio analysis are further disclosed in the rest of the disclosure.

7. Hair Status and Additional Actions

In some embodiments, the devices, systems, and methods disclosed herein can be used to monitor the hair status of the hair.

In certain embodiments, the hair status, at least in part, refers to the hair density of the subject. The hair density can be related to the subject's health status and/or specific conditions such as baldness. In certain embodiments, the hair density can be related to personal hygiene, dieting habits, and environmental conditions.

In certain embodiments, the hair status, at least in part, refers to the hair color of the subject. In certain embodiments, the hair color can be related to a subject's race, ethnicity, and aesthetic appeal.

In certain embodiments, the hair status, at least in part, refers to the hair smoothness of the subject. In certain embodiments, the hair smoothness can be related to a subject's health status, personal hygiene, dieting habits, and environmental conditions.

In certain embodiments, the hair status, at least in part, refers to the hair texture of the subject. In certain embodiments, the hair texture can be related to the subject's race, ethnicity, health status, personal hygiene, dieting habits, and environmental conditions.

In certain embodiments, the hair status, at least in part, refers to the hair thickness of the subject. In certain embodiments, the hair thickness can be related to the subject's health status, personal hygiene, dieting habits, and environmental conditions.

In certain embodiments, the hair status, at least in part, refers to the hair curliness of the subject. In certain embodiments, the hair curliness can be related to the subject's race, ethnicity, health status, personal hygiene, dieting habits, and environmental conditions.

In certain embodiments, the hair status, at least in part, refers to the hair volume of the subject. In certain embodiments, the hair volume can be related to the subject's health status, personal hygiene, dieting habits, and environmental conditions.

In some embodiments, after the hair status is determined, a suitable hair care product for the subject can be determined and/or recommended. In some embodiments, the mobile device can be used to display information related to the suitable hair care product.

In some embodiments, the processed results and/or images of hairs are sent to a third party, i.e., a medical professional. In some embodiments, the processed results and/or images of hairs are stored locally or in a cloud network.

8. Application

The present invention has applications in (a) monitoring the hair status of a subject and providing a recommendation and/or suggestion; (b) detection, purification, and quantification of chemical compounds or biomolecules that are present in a hair sample; and (c) analyzing hair residues in the environment and/or specific niches.

Other Specification Of Present Invention

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, for their entities and for all purpose.

The exemplary embodiments disclosed herein can be combined with the bio/chemical devices, systems and methods including, but not limited to, the devices, systems, and methods as disclosed, described, and/or referred to in the following patent applications:

PCT Application No. PCT/US16/45437, which was filed on Aug. 10, 2016,

PCT Application No. PCT/US16/51775, which was filed on Sep. 14, 2016,

PCT Application No. PCT/US16/51794, which was filed on Sep. 14, 2016,

PCT Application No. PCT/US17/65440, which was filed on Dec. 8, 2017,

U.S. Provisional Application No. 62/369,181, which was filed on Jul. 31, 2016,

U.S. Provisional Application No. 62/394,753, which was filed on Sep. 15, 2016,

U.S. Provisional Application No. 62/412,006, which was filed on Oct. 24, 2016,

U.S. Provisional Application No. 62/431,639, which was filed on Dec. 9, 2016,

U.S. Provisional Application No. 62/437,339, which was filed on Dec. 21, 2016,

U.S. Provisional Application No. 62/456,065, which was filed on Feb. 7, 2017,

U.S. Provisional Application No. 62/456,488, which was filed on Feb. 8, 2017,

U.S. Provisional Application No. 62/456,287, which was filed on Feb. 8, 2017,

U.S. Provisional Application No. 62/456,528, which was filed on Feb. 8, 2017,

U.S. Provisional Application No. 62/456,537, which was filed on Feb. 8, 2017,

U.S. Provisional Application No. 62/456,612, which was filed on Feb. 8, 2017,

U.S. Provisional Application No. 62/456,631, which was filed on Feb. 8, 2017,

U.S. Provisional Application No. 62/456,596, which was filed on Feb. 8, 2017,

U.S. Provisional Application No. 62/456,590, which was filed on Feb. 8, 2017,

U.S. Provisional Application No. 62/456,638, which was filed on Feb. 8, 2017,

U.S. Provisional Application No. 62/456,598, which was filed on Feb. 8, 2017,

U.S. Provisional Application No. 62/456,552, which was filed on Feb. 8, 2017,

U.S. Provisional Application No. 62/456,603, which was filed on Feb. 8, 2017,

U.S. Provisional Application No. 62/456,585, which was filed on Feb. 8, 2017,

U.S. Provisional Application No. 62/456,628, which was filed on Feb. 8, 2017,

U.S. Provisional Application No. 62/456,504, which was filed on Feb. 8, 2017,

U.S. Provisional Application No. 62/456,988, which was filed on Feb. 9, 2017,

U.S. Provisional Application No. 62/457,084, which was filed on Feb. 9, 2017,

U.S. Provisional Application No. 62/457,031, which was filed on Feb. 9, 2017,

U.S. Provisional Application No. 62/456,904, which was filed on Feb. 9, 2017,

U.S. Provisional Application No. 62/457,075, which was filed on Feb. 9, 2017,

U.S. Provisional Application No. 62/457,009, which was filed on Feb. 9, 2017,

U.S. Provisional Application No. 62/457,133, which was filed on Feb. 9, 2017,

U.S. Provisional Application No. 62/457,103, which was filed on Feb. 9, 2017,

U.S. Provisional Application No. 62/459,267, which was filed on Feb. 15, 2017,

U.S. Provisional Application No. 62/459,303, which was filed on Feb. 15, 2017,

U.S. Provisional Application No. 62/459,337, which was filed on Feb. 15, 2017,

U.S. Provisional Application No. 62/459,232, which was filed on Feb. 15, 2017,

U.S. Provisional Application No. 62/459,160, which was filed on Feb. 15, 2017,

U.S. Provisional Application No. 62/459,972, which was filed on Feb. 16, 2017,

U.S. Provisional Application No. 62/459,496, which was filed on Feb. 15, 2017,

U.S. Provisional Application No. 62/459,554, which was filed on Feb. 15, 2017,

U.S. Provisional Application No. 62/459,598, which was filed on Feb. 15, 2017,

U.S. Provisional Application No. 62/460,047, which was filed on Feb. 16, 2017,

U.S. Provisional Application No. 62/460,083, which was filed on Feb. 16, 2017,

U.S. Provisional Application No. 62/460,076, which was filed on Feb. 16, 2017,

U.S. Provisional Application No. 62/460,062, which was filed on Feb. 16, 2017,

U.S. Provisional Application No. 62/459,920, which was filed on Feb. 16, 2016,

U.S. Provisional Application No. 62/459,577, which was filed on Feb. 15, 2017,

U.S. Provisional Application No. 62/459,602, which was filed on Feb. 15, 2017,

U.S. Provisional Application No. 62/460,069, which was filed on Feb. 16, 2017,

U.S. Provisional Application No. 62/460,088, which was filed on Feb. 16, 2017,

U.S. Provisional Application No. 62/460,091, which was filed on Feb. 16, 2017,

U.S. Provisional Application No. 62/460,757, which was filed on Feb. 18, 2017,

U.S. Provisional Application No. 62/463,578, which was filed on Feb. 24, 2017,

U.S. Provisional Application No. 62/488,684, which was filed on Apr. 21, 2017; and U.S. Provisional Application No. 62/597,851, which was filed on Dec. 12, 2017 which are all hereby incorporated in reference by their entireties for all purpose.

9. QMAX Device

The devices, systems, and methods herein disclosed can include or use a QMAX device, which can comprise plates and optionally spacers. In some embodiments, the dimension of the individual components of the QMAX device and its adaptor are listed, described and/or summarized in PCT Application No. PCT/US16/45437 filed on Aug. 10, 2016, and U.S. Provisional Application Nos. 62,431,639 filed on Dec. 9, 2016 and 62/456,287 filed on Feb. 8, 2017, which are all hereby incorporated by reference by their entireties.

A. Q-Card

The devices, systems, and methods disclosed herein can include or use Q-cards for sample detection, analysis, and quantification. Details of the QMAX card are described in detail in a variety of publications including International Application No. PCT/US2016/046437 (Essenlix Docket No. ESSN-028WO), which is hereby incorporated by reference herein for all purposes.

Generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) ae used for the plate to achieve certain objectives.

In certain embodiments, the two plates can have the same or different parameters for each of the following parameters: plate material, plate thickness, plate shape, plate area, plate flexibility, plate surface property, and plate optical transparency.

The plates can be made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1: The inorganic materials for the plates include, not limited to, glass, quartz, oxides, silicon-dioxide, silicon-nitride, hafnium oxide (HfO), aluminum oxide (AlO), semiconductors: (silicon, GaAs, GaN, etc.), metals (e.g., gold, silver, coper, aluminum, Ti, Ni, etc.), ceramics, or any combinations of thereof.

Mat-2: The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyimide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain embodiments, the plates are each independently made of at least one of glass, plastic, ceramic, and metal. In certain embodiments, each plate independently includes at least one of glass, plastic, ceramic, and metal. In certain embodiments, one plate is different from the other plate in lateral area, thickness, shape, materials, or surface treatment. In certain embodiments, one plate is the same as the other plate in lateral area, thickness, shape, materials, or surface treatment.

The materials for the plates can be rigid, flexible or any flexibility between the two. The rigid (i.e. stiff) or flexibility is relative to a give pressing forces used in bringing the plates into the closed configuration.

In certain embodiments, at least one of the two plates are transparent (to a light). In certain embodiments at least, a part or several parts of one plate or both plates are transparent. In certain embodiments, the plates are non-transparent.

In certain embodiments, the average thicknesses for at least one of the pates are 2 nm or less, 10 nm or less, 100 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, or a range between any two of the values.

In certain embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In certain embodiments, the thickness of a plate is not uniform across the plate. Using a different plate thickness at different location can be used to control the plate bending, folding, sample thickness regulation, and others.

Generally, the plates can have any shapes, as long as the shape allows a compress open flow of the sample and the regulation of the sample thickness. However, in certain embodiments, a particular shape may be advantageous. The shape of the plate can be round, elliptical, rectangles, triangles, polygons, ring-shaped, or any superpositions of these shapes.

In certain embodiments, the two plates can have the same size or shape, or different. The area of the plates depends on the application. In certain embodiments, at least one of the plates is in the form of a belt (or strip) that has a width, thickness, and length.

In certain embodiments, the two surfaces of the plate are significantly parallel with each other. In certain embodiments, the two surfaces of the plate are not parallel with each other.

In certain embodiments, a plate is flexible under the compressing of a CROF process. In certain embodiments, both plates are flexible under the compressing of a CROF process.

In certain embodiments, a plate is rigid and another plate is flexible under the compressing of a CROF process. In certain embodiments, both plates are rigid. In certain embodiments, both plates are flexible but have different flexibility.

In certain embodiments, a plate is optical transparent. In certain embodiments, both plates are optical transparent. In certain embodiments, a plate is optical transparent and another plate is opaque. In certain embodiments, both plates are opaque. In certain embodiments, both plates are optical transparent but have different optical transparency. The optical transparency of a plate can refers to a part or the entire area of the plate.

B. Spacers

In an embodiment, the present QMAX device can have spacers. Generally, the spacers are configured to have one or any combinations of the following functions and properties: the spacers are configured to (1) control, together with the plates, the thickness of the sample or a relevant volume of the sample (preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) can be a single spacer or a plurality of spacers. (e.g. an array). Certain embodiments of a plurality of spacers is an array of spacers (e.g. pillars), where the inter-spacer distance is periodic or aperiodic, or is periodic or aperiodic in certain areas of the plates, or has different distances in different areas of the plates.

In certain embodiments, the lateral shapes of the pillar spacers include a shape selected from the group consisting of round, elliptical, rectangles, triangles, polygons, ring-shaped, star-shaped and letter-shaped (e.g. L-shaped, C-shaped, the letters from A to Z). In certain embodiments, the shapes of the spacers have rounded corners. For example, a rectangle shaped spacer has one, several or all corners rounded (like a circle rather 90-degree angle). A round corner often make a fabrication of the spacer easier, and in some cases less damage to a biological material.

The sidewall of the pillars can be straight, curved, sloped, or different shaped in different section of the sidewall. In certain embodiments, the spacers are pillars of various lateral shapes, sidewalls, and pillar-height to pillar lateral area ratio. In a preferred embodiment, the spacers have shapes of pillars for allowing open flow.

Generally, the spacers can be made of any material that is capable of being used to regulate, together with the two plates, the thickness of a relevant volume of the sample. In certain embodiments, the materials for the spacers are different from that for the plates. In certain embodiments, the materials for the spaces are at least the same as a part of the materials for at least one plate. The spacers can be made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

In certain embodiments, all spacers have the same pre-determined height. In certain embodiments, spacers have different pre-determined height. The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or a range between any two of the values.

The spacers can be a single spacer or a plurality of spacers on the plate or in a relevant area of the sample. In certain embodiments, the spacers on the plates are configured and/or arranged in an array form, and the array is a periodic, non-periodic array or periodic in some locations of the plate while non-periodic in other locations. In certain embodiments, the periodic array of the spacers has a lattice of square, rectangle, triangle, hexagon, polygon, or any combinations of thereof, where a combination means that different locations of a plate has different spacer lattices. In certain embodiments, the inter-spacer distance of a spacer array is periodic (i.e. uniform inter-spacer distance) in at least one direction of the array. In certain embodiments, the inter-spacer distance is configured to improve the uniformity between the plate spacing at a closed configuration.

The distance between neighboring spacers (i.e. the inter-spacer distance) is 1 µm or less, 5 µm or less, 10 µm or less, 20 µm or less, 30 µm or less, 40 µm or less, 50 µm or less, 60 µm or less, 70 µm or less, 80 µm or less, 90 µm or less, 100 µm or less, 200 µm or less, 300 µm or less, 400 µm or less, or a range between any two of the values.

The spacers can be fabricated on a plate in a variety of ways, using lithography, etching, embossing (nanoimprint), depositions, lift-off, fusing, or a combination of thereof. In certain embodiments, the spacers are directly embossed or imprinted on the plates. In certain embodiments, the spacers imprinted into a material (e.g. plastics) that is deposited on the plates. In certain embodiments, the spacers are made by directly embossing a surface of a CROF plate. The nano-imprinting may be done by roll to roll technology using a roller imprinter, or roll to a planar nanoimprint. Such process has a great economic advantage and hence lowering the cost.

In certain embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom exposes the plate surface and then a spacer material is deposited into the hole and afterwards the removable material is removed, leaving only the spacers on the plate surface. In certain embodiments, the spacers deposited on the plate are fused with the plate. In certain embodiments, the spacer and the plates are fabricated in a single process. The single process includes imprinting (i.e. embossing, molding) or synthesis.

In certain embodiments, at least two of the spacers are fixed to the respective plate by different fabrication methods, and optionally wherein the different fabrication methods include at least one of being deposition, bonded, fuse, imprinted, and etched.

In certain embodiments, one or more of the spacers are fixed to the respective plate(s) is by a fabrication method of being bonded, being fused, being imprinted, or being etched, or any combination of thereof.

In certain embodiments, the fabrication methods for forming such monolithic spacers on the plate include a method of being bonded, being fused, being imprinted, or being etched, or any combination of thereof.

C. Method of Manufacture of QMAX Cards

Details of the method of QMAX card manufacture are described in detail in a variety of publications including International Application No. PCT/US2018/057873 filed Oct. 26, 2018, which is hereby incorporated by reference herein for all purposes.

Devices of the disclosure may be fabricated using techniques well known in the art. The choice of fabrication technique will depend on the material used for the device and the size of the spacer array and/or the size of the spacers. Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small spacers and large aspect ratios (ratio of spacer height to lateral dimension). Thermoforming (embossing, injection molding) of plastic devices may also be used, e.g., when the smallest lateral feature is >20 microns and the aspect ratio of these features is ≤10.

Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) may be employed. Techniques such as laser nicromachining may be adopted for plastic materials with high photon absorption efficiency. This technique is suitable for lower throughput fabrication because of the serial nature of the process. For mass-produced plastic devices, thermoplastic injection molding, and compression molding may be suitable. Conventional thermoplastic injection molding used for mass-fabrication of compact discs (which preserves fidelity of features in sub-microns) may also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) has the advantages of being compatible with high molecular weight polymers, which are excellent for small structures and may replicate high aspect ratio structures but has longer cycle times. Injection molding works well for low aspect ratio structures and is most suitable for low molecular weight polymers.

A device may be fabricated in one or more pieces that are then assembled. Layers of a device may be bonded together by clamps, adhesives, heat, anodic bonding, or reactions between surface groups (e.g., wafer bonding). Alternatively, a device with channels or gaps in more than one plane may be fabricated as a single piece, e.g., using stereolithography or other three-dimensional fabrication techniques.

In certain embodiments of the present disclosure, a method for fabricating any Q-Card of the present disclosure can comprise injection molding of the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise Laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise injection molding and laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise nanoimprinting or extrusion printing to fabricated both the first and the second plate. In certain embodiments of the present disclosure, a method for fabricating any Q-Card of the present disclosure can comprise fabricating the first plate or the second plate, using injection molding, laser cutting the first plate, nanoimprinting, extrusion printing, or a combination of thereof. In certain embodiments of the present disclosure, a method for fabricating any Q-Card of the present disclosure can comprise a step of attaching the hinge on the first and the second plates after the fabrication of the first and second plates.

D. Hinges, Opening Notches, Recessed Edges, Sliders, and Grooves

The devices, systems, and methods disclosed herein, can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/431,639, which was filed on Dec. 9, 2016, U.S. Provisional Application No. 62/456,065, which was filed on Feb. 7, 2017, U.S. Provisional Application Nos. 62/456,287 and 62/456,504, which was filed on Feb. 8, 2017, and U.S. Provisional Application No. 62/539,660, which was filed on Aug. 1, 2017, all of which applications are incorporated herein in their entireties for all purposes.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

In some embodiments, the second plate of the QMAX device comprises a groove, wherein the second plate with the groove can accommodate at least one strand of hair and restrict the movement of the at least one strand of hair. In additional embodiments, the at least one strand of hair is placed in the groove of the second plate by rubbing a plurality of hairs by hand to position the at least one strand of hair in the groove. In some instances, the preferred dimensions of the groove are 50 µm×50 µm, which can accommodate one strand of hair.

10. Adaptor

Details of the Adaptor are described in detail in a variety of publications including International Application No. PCT/US2018/017504 (Essenlix Docket No. ESXPCT18F04), which is hereby incorporated by reference herein for all purposes.

The present invention that is described herein address this problem by providing a system comprising an optical adaptor and a smartphone. The optical adaptor device fits over a smartphone converting it into a microscope which can take bright-field images of the hair sample. This system can be operated conveniently and reliably by a common person at any location. The optical adaptor takes advantage of the existing resources of the smartphone, including camera, light source, processor and display screen, which provides a low-cost solution let the user to do bright-field microscopy.

The optical adaptor device can comprise a holder frame fitting over the upper part of the smartphone and an optical box attached to the holder having sample receptacle slot and illumination optics. In some references (U.S. Pat. No. 2016/029091 and U.S. Pat. No. 2011/0292198), their optical adaptor design is a whole piece including both the clip-on mechanics parts to fit over the smartphone and the functional optics elements. This design has the problem that they need to redesign the whole-piece optical adaptor for each specific model of smartphone. But in this present invention, the optical adaptor is separated into a holder frame only for fitting a smartphone and a universal optical box containing all the functional parts. For the smartphones with different dimensions, as long as the relative positions of the camera and the light source are the same, only the holder frame need to be redesigned, which will save a lot of cost of design and manufacture.

The optical box of the optical adaptor comprises: a receptacle slot which receives and position the sample in a sample slide in the field of view and focal range of the smartphone camera; a bright-field illumination optics for capturing bright-field microscopy images of a sample.

The receptacle slot has a rubber door attached to it, which can fully cover the slot to prevent the ambient light getting into the optical box to be collected by the camera. In U.S. Pat. 2016/0290916, the sample slot is always exposed to the ambient light which won't cause too much problem because it only does bright-field microscopy.

For all common smartphones, however, the optical filter putting in front of the camera cannot block the undesired wavelength range of the light emitted from the light source of a smartphone very well due to the large divergence angle of the beams emitted by the light source and the optical filter not working well for un-collimated beams. Collimation optics can be designed to collimated the beam emitted by the smartphone light source to address this issue, but this approach increase the size and cost of the adaptor. Instead, in this present invention, fluorescent illumination optics enables the excitation light to illuminate the sample partially from the waveguide inside the sample slide and partially from the backside of the sample side in large oblique incidence angle so that excitation light will nearly not be collected by the camera to reduce the noise signal getting into the camera.

In one embodiment, the bright-field illumination optics in the adaptor receive and turn the beam emitted by the light source so as to back-illuminated the sample in normal incidence angle.

Typically, the optical box also comprises a lens mounted in it aligned with the camera of the smartphone, which magnifies the images captured by the camera. The images captured by the camera can be further processed by the processor of smartphone and outputs the analysis result on the screen of smartphone.

A sample slider is mounted inside the receptacle slot to receive the QMAX device and position the sample in the QMAX device in the field of view and focal range of the smartphone camera. The sample slider comprises a fixed track frame and a moveable arm. The frame track is fixedly mounted in the receptacle slot of the optical box. And the track frame has a sliding track slot that fits the width and thickness of the QMAX device so that the QMAX device can slide along the track. The width and height of the track slot is carefully configured to make the QMAX device shift less than 0.5 mm in the direction perpendicular to the sliding direction in the sliding plane and shift less than less than 0.2 mm along the thickness direction of the QMAX device. The frame track has an opened window under the field of view of the camera of smartphone to allow the light back-illuminate the sample. A moveable arm can be pre-built in the sliding track slot of the track frame and moves together with the QMAX device to guide the movement of QMAX device in the track frame.

The moveable arm equipped with a stopping mechanism with two pre-defined stop positions. For one position, the arm will make the QMAX device stop at the position where a fixed sample area on the QMAX device is right under the camera of smartphone. For the other position, the arm will make the QMAX device stop at the position where the sample area on QMAX device is out of the field of view of the smartphone and the QMAX device can be easily taken out of the track slot.

The moveable arm switches between the two stop positions by a pressing the QMAX device and the moveable arm together to the end of the track slot and then releasing. The moveable arm can indicate if the QMAX device is inserted in correct direction. The shape of one corner of the QMAX device is configured to be different from the other three right angle corners. And the shape of the moveable arm matches the shape of the corner with the special shape so that only in correct direction can QMAX device slide to correct position in the track slot.

The devices, systems, and methods disclosed herein can include or use Q-cards for sample detection, analysis, and quantification. In some embodiments, the Q-card is used together with an adaptor that is configured to accommodate the Q-card and connect to a mobile device so that the sample in the Q-card can be imaged, analyzed, and/or measured by the mobile device. The structure, material, function, variation, dimension, and connection of the Q-card, the adaptor, and the mobile are disclosed herein, listed, described, and/or summarized in PCT Application Nos. PCT/US16/45437 and PCT/US16/51775, which were filed on Aug. 10, 2016 and Sep. 14, 2016, respectively, and U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g., a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample.

11 Smartphone Detection System

The devices, systems, and methods disclosed herein can include or use Q-cards for sample detection, analysis, and quantification. In some embodiments, the Q-card is used together with an adaptor that can connect the Q-card with a smartphone detection system. In some embodiments, the smartphone comprises a camera and/or an illumination source The smartphone detection system, as well the associated hardware and software are herein disclosed, listed, described, and/or summarized in PCT Application Nos. PCT/US16/045437 and PCT/US16/051775, which were respectively filed on Aug. 10, 2016 and Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application No. 62/460,075 and 62/459,920, which were filed on Feb. 16, 2017, all of which are incorporated herein in their entireties for all purposes.

In some embodiments, the smartphone comprises a camera, which can be used to capture images or the sample when the sample is positioned in the field of view of the camera (e.g., by an adaptor). In certain embodiments, the camera includes one set of lenses (e.g., as in iPhone™ 6). In certain embodiments, the camera includes at least two sets of lenses (e.g., as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

12. Dimensions

The devices, systems, and methods herein disclosed can include or use a QMAX device, which can comprise plates and spacers. In some embodiments, the dimension of the individual components of the QMAX device and its adaptor are listed, described and/or summarized in PCT Application No. PCT/US16/45437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

In some embodiments, the dimensions are listed in the Tables below:

| | A. Plates | |
|---|---|---|
| Parameters | Embodiments | Preferred Embodiments |
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 µm or less, 200 µm or less, 500 µm or less, 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 µm (micron) or less, 5 µm or less, 10 µm or less, 20 µm or less, 50 µm or less, 100 µm or less, 150 µm or less, 200 µm or less, 300 µm or less, 500 µm or less, 800 µm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |

| A. Plates | | |
|---|---|---|
| Parameters | Embodiments | Preferred Embodiments |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm$^2$; or around 750 mm$^2$. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 μm or less, 10 μm or less, 20 μm or less, 30 μm or less, 40 μm or less, 50 μm or less, 100 μm or less, 200 μm or less, 300 μm or less, 400 μm or less, 500 μm or less, 1 mm or less, 7500 μm or less, 1 mm or less, 5 mm or less, 10 mm or less, 100 mm or less, or 1000 mm or less, or in a range between any two of these values. | In the range of 1 mm to 10 mm; Or About 5 mm |

| B. Hinge | | |
|---|---|---|
| Parameters | Embodiments | Preferred Embodiments |
| Number Length of Hinge Joint | 1, 2, 3, 4, 5, or more 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | 1 or 2 In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm$^2$ or less, 5 mm$^2$ or less, 10 mm$^2$ or less, 20 mm$^2$ or less, 30 mm$^2$ or less, 40 mm$^2$ or less, 50 mm$^2$ or less, 100 mm$^2$ or less, 200 mm$^2$ or less, 500 mm$^2$ or less, or in a range between any of the two values | In the range of 20 to 200 mm$^2$; or about 120 mm$^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree (in degrees) | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 μm or less, 1 μm or less, 2 μm or less, 3 μm or less, 5 μm or less, 10 μm or less, 20 μm or less, 30 μm or less, 50 μm or less, 100 μm or less, 200 μm or less, 300 μm or less, 500 μm or less, 1 mm or less, 2 mm or less, and a range between any two of these values | In the range of 20 μm to 1 mm; or Around 50 μm |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

| C. Notch | | |
|---|---|---|
| Parameters | Embodiments | Preferred Embodiments |
| Number Shape | 1, 2, 3, 4, 5, or more round, ellipse, rectangle, triangle, polygon, ring-shaped, or any superposition or portion of these shapes. | 1 or 2 Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 mm$^2$ (square millimeter) or less, 10 mm$^2$ or less, 25 mm$^2$ or less, 50 mm$^2$ or less, 75 mm$^2$ or less or in a range between any two of these values. | In the range of 10 to 150 mm$^2$; or about 50 mm$^2$ |

D. Trench

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 $mm^2$ or less, 0.005 $mm^2$ or less, 0.01 $mm^2$ or less, 0.05 $mm^2$ or less, 0.1 $mm^2$ or less, 0.5 $mm^2$ or less, 1 $mm^2$ or less, 2 $mm^2$ or less, 5 $mm^2$ or less, 10 $mm^2$ or less, 20 $mm^2$ or less, or in a range between any two of these values. | |
| Volume | 0.1 uL or more, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

E. Receptable Slot

| Parameters | Embodiments | Preferred Embodiments |
|---|---|---|
| Shape of receiving area | round, ellipse, rectangle, triangle, polygon, ring-shaped, or any superposition of these shapes; | |
| Difference between sliding track | 100 nm, 500 nm, 1 µm, 2 µm, 5 µm, 10 µm, 50 µm, 100 µm, 300 µm, 500 µm, 1 mm, 2 mm, 5 mm, 1 cm, or in a range between any two of the values. | In the range of 50 to 300 µm; or about 75 µm |
| gap size and card thickness | | |
| Difference between receiving area and card area | 1 $mm^2$ (square millimeter) or less, 10 $mm^2$ or less, 25 $mm^2$ or less, 50 $mm^2$ or less, 75 $mm^2$ or less, 1 $cm^2$ (square centimeter) or less, 2 $cm^2$ or less, 3 $cm^2$ or less, 4 $cm^2$ or less, 5 $cm^2$ or less, 10 $cm^2$ or less, 100 $cm^2$ or less, or in a range between any of the two values. | |

9. Cloud

The devices, systems, and methods disclosed can employ cloud technology for data transfer, storage, and/or analysis. The related cloud technologies are herein disclosed, listed, described, and/or summarized in PCT Application (designating U.S.) Nos. PCT/US16/45437 and PCT/US16/51775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all applications which are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g., smartphone) can be connected to the cloud through any type of network, including a local area network (LAN) or a wide area network (WAN).

In some embodiments, the data (e.g., images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

Other Examples of the Present Invention

A1. A device for monitoring hair status of a subject, comprising:

(a) a hair holder that is configured to accommodate a plurality of hairs and restrict the movement of the hairs, wherein the hair holder comprises a liquid material that is in contact with the hairs; and (b) an adaptor that connects the hair holder to a mobile device, wherein, the adaptor positions the plurality of hairs in the hair holder in a field of view of an imager, wherein, the imager is a part of or the entirety of the mobile device and can capture, analyze, or digitally transmit images of the hairs or processed results of the images of the hairs to a remote third party for further analysis.

CR1. A device for monitoring hair status of a subject, comprising:

(a) a hair holder with at least one groove to accommodate a plurality of hairs and restrict the movement of the plurality of hairs, wherein the hair holder comprises a liquid material that is in contact with the plurality of hairs; and (b) an adaptor that connects the hair holder to a mobile device, wherein, the adaptor, positions the plurality of hairs in the view field of an imager, wherein, the imager is a part of or is the entirety of the mobile device.

CR2. A system for rapidly analyzing the hair status of a subject using a mobile device, comprising:

(a) a hair holder with at least one groove to accommodate a plurality of hairs and to restrict the movement of the plurality of hairs, wherein, the hair holder comprises a liquid material that is in contact with the plurality of hairs, (b) an adaptor that connects the hair holder to a mobile device; and (c) a mobile device comprising an imager, wherein the imager is a part of or the entirety of the mobile device and can capture, analyze, or digitally transmit images of the hairs or processed results of the images of the hairs to a remote third party for further analysis.

A2. A method of monitoring the hair status of a subject, comprising:

(a) obtaining a hair holder that is configured to accommodate a plurality of hairs and restrict the movement of the plurality of hairs, (b) obtaining an adaptor that connects a hair holder to a mobile device, (c) placing the plurality of hairs in the hair holder and connecting the hair holder into the adaptor, wherein the hair holder further comprises a liquid material that is in contact with the plurality of hairs, (d) attaching the adaptor to the mobile device, (e) capturing images of the plurality of hairs in the hair holder with an imager, wherein, the imager is a part of or the entirety of the mobile device and can capture, analyze, or digitally transmit images of the hairs or processed results of the images of the hairs to a remote third party for further analysis.

A3. A method of monitoring hair status of a subject, comprising:

(a) obtaining a hair holder that comprises a first plate and a second plate with a groove, wherein the second plate with groove is configured to accommodate one or more strands of hair, (b) placing one or more strands of hair on the second plate with a groove and rubbing the one or more strands of hair by hand into groove, (d) closing the first plate and second plate with a groove and connecting the hair holder to an adaptor, (e) attaching the adaptor to the mobile device; and (f) capturing images of the plurality of hairs in the hair holder with an imager, wherein, the imager is a part of or the entirety of the mobile device and can capture, analyze, or digitally transmit images of the hairs or processed results of the images of the hairs to a remote third party for further analysis.

CR3. A method of monitoring the hair status of a subject, comprising:

(a) obtaining a hair holder that is configured to accommodate a plurality of hairs wherein the hair holder has at least one groove to restrict the movement of hairs;

(b) obtaining an adaptor that is configured to connect the hair holder to a mobile device;

(c) placing the plurality of hairs in the hair holder and inserting the hair holder into the adaptor, wherein the hair holder comprises a liquid material that is in contact with the plurality of hairs, (d) attaching the adaptor to the mobile device; and (e) capturing images of the plurality of hairs in the hair holder with an imager, wherein, the imager is a part of or the entirety of the mobile device and can capture, analyze, or digitally transmit images of the hairs or processed results of the images of the hairs to a remote third party for further analysis.

CR4. A method of monitoring the hair status of a subject, comprising:

(a) obtaining a hair holder that comprises a first plate and a second plate, wherein at least one of the plates comprises at least one groove configured to accommodate a plurality of hairs, (b) placing a plurality of hairs on one of the plates with a groove, and rubbing at least one strand of hair from the plurality of hairs by hand to position at least one strand of hair in the groove;

(c) obtaining an adaptor that connects the hair holder to a mobile device (d) closing the plates and inserting the plates into the adaptor;

(e) attaching the adaptor to the mobile device; and (f) capturing images of the plurality of hairs in the hair holder with an imager, wherein, the imager is a part of or the entirety of the mobile device and can capture, analyze, or digitally transmit images of the hairs or processed results of the images of the hairs to a remote third party for further analysis.

B1.1 The devices, systems, or methods of any prior embodiments, wherein the subject is a mammal.

B1.2 The devices, systems, or methods of any prior embodiments, wherein the subject is a human.

B1.3 The devices, systems, or methods of any prior embodiments, wherein the subject is suffering from a disease or condition that affects hair quality or hair amount.

B1.4 The devices, systems, or methods of any prior embodiments, wherein the subject is suffering from a disease or condition that causes baldness.

B1.5 The devices, systems, or methods of any prior embodiments, wherein the subject is a human that is suffering from a disease or condition that affects hair quality or hair amount.

B4.1 The devices, systems, or methods of any prior embodiments, wherein the hair holder comprises a first plate and a second plate, wherein the two plates are configured to be capable of being pressed together and restrict the movement of the hairs.

B4.2 The devices, systems, or methods of any prior embodiments, wherein the hair holder comprises a first plate and a second plate, wherein the two plates are configured to be capable of being pressed together with a uniform gap between the plates, wherein the gap accommodates the hairs.

B4.3 The devices, systems, or methods of any prior embodiments, wherein the hair holder is a part of or the entirety of a QMAX device.

B3.7 The devices, systems, or methods of any prior embodiments, wherein the hair holder comprises a first plate and a second plate, where one of the plates comprises a groove configured to accommodate the hair strands.

CR4. The devices, systems, or methods of any prior embodiments, wherein the hair holder with at least one strand of hair comprise a liquid material that is in contact with a least one strand of hair.

B5.1 The devices, systems, or methods of any prior embodiments, wherein the liquid material is water.

B5.2 The devices, systems, or methods of any prior embodiments, wherein the liquid material is a glue.

B5.3 The devices, systems, or methods of any prior embodiments, wherein the liquid material is positioned between the plates and in contact with at least one strand of hair.

A3.1 The devices, systems, or methods of any prior embodiments, wherein the liquid material that is in contact with at least one strand of hair is added before closing the two plates.

B3.1 The devices, systems, or methods of any prior embodiments, wherein the adaptor comprises optical elements that are configured to optimize capturing the image of the target area.

B3.2 The devices, systems, or methods of any prior embodiments, wherein the optical elements comprise an internal lens.

B3.3 The devices, systems, or methods of any prior embodiments, wherein the optical elements comprise an illumination re-distributor that is positioned before a light source in the camera.

B3.4 The devices, systems, or methods of any prior embodiments, wherein the illumination re-distributor is configured to re-distribute the light from the light source, providing even illumination of the target area.

B3.5 The devices, systems, or methods of any prior embodiments, wherein the adaptor comprises a stabilizing structure that is configured to removably attached to the body part.

B3.6 The devices, systems, or methods of any prior embodiments, wherein the adaptor comprises a light shielding cover that is configured to shield the target area from ambient light.

B2.1 The devices, systems, or methods of any prior embodiments, wherein the mobile device is a smartphone.

B2.2 The devices, systems, or methods of any prior embodiments, wherein the mobile device further comprises a light source.

A2.3. The devices, systems, or methods of any prior embodiments, wherein the image is captured with illumination from the light source in the adaptor.

A6.1. The devices, systems, or methods of any prior embodiments, further comprising analyzing hair quality and determining a suitable hair care product for the subject.

A6.1. The devices, systems, or methods of any prior embodiments, further comprising displaying information related to the suitable hair care product on the mobile device.

A6.3. The devices, systems, or methods of any prior embodiments, wherein the processed results and/or images are sent to third party that is a medical professional.

A6.4. The devices, systems, or methods of any prior embodiments, wherein the processed results and/or images are stored locally or in a cloud network.

A6.5. The devices, systems, or methods of any prior embodiments, further comprising determining local hair density in a hair growing area on the subject's body.

A6.6. The devices, systems, or methods of any prior embodiments, further comprising analyzing hair density and determining a suitable hair growing product for the subject.

A7.1. The devices, systems, or methods of any prior embodiments, wherein the hair status includes one or more traits consisting of: hair density, hair color, hair smoothness, hair texture, hair thickness, hair curliness, and hair volume.

A7.2. The devices, systems, or methods of any prior embodiments, wherein the hair status includes all traits of: hair density, hair color, hair smoothness, hair texture, hair thickness, hair curliness, and hair volume.

A7.3. The devices, systems, or methods of any prior embodiments, wherein the hair status includes the traits of: hair density, hair texture, and hair volume.

A7.4. The devices, systems, or methods of any prior embodiments, wherein the hairs are connected to the subject.

A7.5. The devices, systems, or methods of any prior embodiments, wherein the hairs are separated from the subject.

Aspects:

1. A device for examining a microfiber, comprising:
    a first plate, a second plate, and a groove, wherein:
        i. the first and second plates are movable relative to each other into different configurations, including an open configuration and a closed configuration;
        ii. the groove is on the surface of the second plate, wherein the groove is configured to accommodate one or a plurality of microfibers, wherein the groove has a depth of 3 mm or less and a length at least 5 mm;
    wherein, in the open configuration, the two plates are configured to be partially or completely separated apart, so that a microfiber sample from a subject is deposited in the groove,
    wherein in the closed configuration, which is configured after the microfiber sample is deposited in the open configuration, the first plate is placed on top of the second plate, covering the groove,
    wherein the position of the groove on the second plate is configured to make at least a part of the microfiber sample placed in the groove being imaged in the field of view of an imager, wherein the imager is configured to view at least a part of the surface of the second plate, and
    wherein the microfiber is a diameter of 500 µm or less and a length of 4 mm or longer.

2. A device for examining a microfiber, comprising:
    a first plate, a second plate, a groove, and spacers, wherein:
        iii. the first and second plates are movable relative to each other into different configurations, including an open configuration and a closed configuration;
        iv. the groove is on an inner surface of the second plate, wherein the groove has a depth of 3 mm or less and a length at least 5 mm;
        v. one or both of the plates comprise the spacers that are fixed on the inner surface of a respective plate, wherein the spacers have a uniform height of 300 µm or less;
    wherein, in the open configuration, the two plates are configured to be partially or completely separated apart, so that a microfiber sample from a subject is deposited in the groove,
    wherein, in the closed configuration, which is configured after the microfiber sample is deposited in the open configuration, the first plate is place on top of the second plate, covering the groove,
    wherein the position of the groove on the second plate is configured to make at least a part of the microfiber sample placed in the groove being imaged in the field of view of an imager, wherein the groove is configured to accommodate one or a plurality of microfibers, wherein the imager is configured to view at least a part of the surface of the second plate,
    wherein in the closed configuration, the spacers regulate the spacing between the inner surface of the plates,
    wherein an inner surface of a plate is the surface of the plate that faces, in a closed configuration, the inner surface of the other plate, and
    wherein the microfiber is a diameter of 500 µm or less and a length of 4 mm or longer.

3. A device, comprising:
    a first plate; and
    a second plate comprising a groove on a surface of the second plate,
    wherein the first plate and the second plate are movable relative to each other into:
        i. an open configuration in which the first plate and the second plate are configured to be partially or completely separated apart such that the groove is capable of receiving a microfiber sample from a subject; and
        ii. a closed configuration, in which the first plate is placed on top of the second plate thereby covering the groove.

4. The device of Aspect 3, wherein the groove has a depth of 3 mm or less and a length at least 5 mm.

5. The device of any of Aspect 3-4, wherein the groove is configured to accommodate one or a plurality of microfibers.

6. The device of any of Aspect 3-5, wherein the position of the groove on the second plate is configured to make at least a part of the microfiber sample placed in the groove being imaged in the field of view of an imager, wherein the imager is configured to view at least a part of the surface of the second plate.

7. The device of any of Aspect 3-6, wherein the microfiber is a diameter of 500 µm or less and a length of 4 mm or longer.

8. A system for examining a microfiber comprising:
    i. the device of any prior Aspect;
    ii. an imager; and
    iii. an adaptor that is configured to fix the relative position between the device and the image, so that at least a part of the microfiber is imaged in the field of the view of the imager.

9. A system for examining micro fiber comprising:
   i. the device of any prior Aspect;
   ii. an imager; and
   iii. an adaptor that (a) is attached to the imager, and (b) configured to make the device slide into the adaptor and locked into a position, and wherein at the locked position, at least a part of the microfiber is imaged in the field of the view of the imager.

10. The system of any prior Aspect, wherein the imager is at least a part of a smartphone.

11. The system of any prior Aspect, wherein the device further comprises a liquid material that is in contact with the microfibers.

12. The system of any prior Aspect, wherein the groove is further configured to restrict the movement of the microfibers.

13. The system of any prior Aspect, further comprising electronics and a computer system to analyze the microfiber.

14. A method of monitoring a microfiber, comprising:
   (a) obtaining a device of any prior Aspect;
   (b) obtaining an imager; and
   (c) attaching an adaptor that is configured to fix the position between the holder and the imager so that at least a part of the microfiber is imaged in the field of the view of the imager.

15. A method of monitoring a microfiber, comprising:
   (a) obtaining a device of any prior Aspect;
   (b) obtaining an imager; and
   (c) attaching an adaptor that is configured to (i) fix the position between the holder and the imager and (ii) make, when the holder is slid into the adaptor, at least a part of the microfiber being imaged in the field of the view of the imager.

16. The method of any prior Aspect, further comprising capturing images of the microfibers in the device with an imager.

17. The method of any prior Aspect, wherein the length of the microfiber is the same or less than that of the groove.

18. The method of any prior Aspect, further comprising chemical, biological and/or physical analysis of the microfiber.

19. The method of any prior Aspect comprising chemical analysis of the microfiber, wherein the chemical analysis of the microfiber comprises measuring the microfiber's PH value, and reactions with one or more chemical reagents.

20. The method of any prior Aspect comprising biological analysis of the microfiber, wherein the biological analysis of the microfiber comprises analysis of a protein, a nucleic acid, a small molecule, a cell, a bacteria, a virus in or on the microfiber.

21. The device, system method of any prior Aspect, wherein the chemical, biological and/or physical analysis of the microfiber comprises fluorescence imaging, bright field optics, dark field optics, an immunoassay, a nucleic acid assay, a colorimetric assay, immunocytochemistry, or spectrophotometric analysis.

22. The device, system method of any prior Aspect, wherein the groove depth is 0.1 µm, 1 µm, 10 µm, 30 µm, 40 µm, 50 µm, 60 µm, 70 µm, 80 µm, 90 µm, 100 µm, 110 µm, 120 µm, 130 µm, 200 µm, 300 µm, 400 µm, 500 µm, 1 mm, or 2 mm.

23. The device, system method of any prior Aspect, wherein the groove width is 1 µm, 10 µm, 30 µm, 40 µm, 50 µm, 60 µm, 70 µm, 80 µm, 90 µm, 100 µm, 110 µm, 120 µm, 130 µm, 200 µm, 300 µm, 400 µm, 500 µm, 1 mm, 2 mm, 3 mm, 5 mm, or 8 mm.

24. The device, system method of any prior Aspect, wherein the groove length is 100 µm, 110 µm, 120 µm, 130 µm, 200 µm, 300 µm, 400 µm, 500 µm, 1 mm, 10 mm, 20 mm, 50 mm, or 80 mm.

25. The device, system method of any prior Aspect, wherein the groove cross-section is round, half-circle, ellipse, square, rectangle, triangle, polygon, ring-shaped, or any superposition thereof, or any shape that accommodating hair strand.

26. The device, system method of any prior Aspect, wherein the microfiber is a natural material, a synthetic material, or a naturally occurring material that is synthetically modified.

27. The device, system method of any prior Aspect, wherein the microfiber is selected from the group consisting of hair, a glass fiber, a glass microfiber, a cellulose fiber, a nitrocellulose fiber, a cellulose acetate fiber, a nylon fiber, a polyolefin fiber, a polyester fiber, a polycarbonate fiber, a polypropylene fiber, a polyvinylidene difluoride fiber, a polyethylene fiber, a polystyrene fiber, a polyurethane fiber, a polyphenylene oxide fiber, a poly(tetrafluoroethylene-co-hexafluoropropylene) fiber, a quartz fiber, a hydrophilic polymer/fiber, fiberglass, silk, spider silk, seed fiber, leaf fiber, bast fiber, fruit fiber, stalk fiber, animal fiber, collagen, keratin, fibroin, wool, cashmere, camel hair, avian fiber, chitin, chitosan, cotton, flax, hemp, jute, natural fiber composites, and any combination thereof.

28. The device, system, or method of any prior Aspect, wherein the microfibers are connected to the subject.

29. The device, system, or method of any prior Aspect, wherein the microfibers are separated from a subject.

30. The device, system, or method of any prior Aspect, wherein the microfiber is hair from a mammal.

31. The device, system, or method of any prior Aspect, wherein the microfiber is hair from a human.

32. The device, system, or method of any prior Aspect, wherein microfiber is hair of a subject, wherein the subject is suffering from a disease or condition that affects hair quality or hair amount.

33. The device, system, or method of any prior Aspect, wherein microfiber is hair of a subject, and wherein the subject is suffering from a disease or condition that causes baldness.

34. The device, system, or method of any prior Aspect, wherein the hair status includes one or more traits consisting of: hair density, hair color, hair smoothness, hair texture, hair thickness, hair curliness, and hair volume.

35. The device, system, or method of any prior Aspect, wherein the hair status includes all traits of: hair density, hair color, hair smoothness, hair texture, hair thickness, hair curliness, and hair volume.

36. The device, system, or method of any prior Aspect, wherein the hair status includes the traits of: hair density, hair texture, and hair volume.

37. The device, system, or method of any prior Aspect, wherein microfiber is hair of a subject, and wherein the subject is a human that is suffering from a disease or condition that affects hair quality or hair amount.

38. The device, system, or method of any prior Aspect, wherein the hair holder comprises a first plate and a second plate, wherein the two plates are configured to be capable of being pressed together and restrict the movement of the hairs.

39. The device, system, or method of any prior Aspect, wherein the hair holder comprises a first plate and a second plate, wherein the two plates are configured to be capable of being pressed together with a uniform gap between the plates, wherein the gap accommodates the hairs.

40. The device, system, or method of any prior Aspect, wherein the hair holder is a part of or the entirety of a QMAX device.

41. The device, system, or method of any prior Aspect, wherein the hair holder comprises a first plate and a second plate, where one of the plates comprises a groove configured to accommodate the hair strands.

42. The device, system, or method of any prior Aspect, wherein the hair holder with at least one strand of hair comprise a liquid material that is in contact with a least one strand of hair.

43. The method of any prior Aspect, wherein the analysis comprising measuring hair density, hair color, hair smoothness, hair texture, hair thickness, hair curliness, and hair volume.

44. The device, system, or method of any prior Aspect, further comprising analyzing hair quality and determining a suitable hair care product for the subject.

45. The device, system, or method of any prior Aspect, further comprising displaying information related to the suitable hair care product on the mobile device.

46. The device, system, or method of any prior Aspect, wherein the processed results and/or images are sent to third party that is a medical professional.

47. The device, system, or method of any prior Aspect, wherein the processed results and/or images are stored locally or in a cloud network.

48. The device, system, or method of any prior Aspect, further comprising determining local hair density in a hair growing area on the subject's body.

49. The device, system, or method of any prior Aspect, further comprising analyzing hair density and determining a suitable hair growing product for the subject.

We claim:

1. A device for examining a microfiber, comprising:
   a first plate, a second plate, and a groove, wherein:
   (i) the first and second plates are movable relative to each other into different configurations, including an open configuration and a closed configuration;
   (ii) the groove is on the surface of the second plate, wherein the groove is configured to accommodate one or a plurality of microfibers, wherein the groove has a depth of 3 mm or less and a length at least 5 mm;
   (iii) a part or the entire area of one or both the plates is transparent;
   wherein, in the open configuration, the two plates are configured to be partially or completely separated apart, so that a microfiber sample from a subject is deposited in the groove,
   wherein in the closed configuration, which is configured after the microfiber sample is deposited in the open configuration, the first plate is placed on top of the second plate, covering the groove,
   wherein the position of the groove on the second plate is configured to make at least a part of the microfiber sample placed in the groove being imaged in the field of view of an imager, wherein the imager is configured to view at least a part of the surface of the second plate, and
   wherein the microfiber is a diameter of 500 µm or less and a length of 4 mm or longer.

2. The device of claim 1, further comprising the spacers on one or both of the plates, wherein the spacers are fixed on the inner surface of a respective plate, wherein the spacers have a uniform height of 300 µm or less.

3. A system for examining a microfiber, comprising:
   (i) the device of claim 1 or 2;
   (ii) an imager that images the microfiber; and
   (iii) an adaptor that is configured to fix the relative position between the device and the imager, so that at least a part of the microfiber is imaged in the field of the view of the imager.

4. The system of claim 3, further comprising an analyzing device that analyzes, using the image, the microfiber.

5. The system of claim 4, wherein the transmitting device transmit the images to a third party that is a medical professional.

6. The system of claim 3, further comprising a transmitting device that transmits the image of the microfiber or processed results of the images of the microfiber to a party at a remote location.

7. The system of claim 3, further comprising a light source.

8. The system of claim 7, wherein the light source is configured to partially illuminate the sample from the waveguide formed by the two plates, and partially illuminate the sample from the backside of the sample side in a large oblique incidence angle, so that light illumination is substantially not be collected by the imager.

9. The system of claim 7, further comprising an optical system so that light illuminates the microfiber from the front side and the back side of the fiber.

10. The system of claim 3, wherein the adaptor is further configured to make the device slide into the adaptor and locked into a position.

11. The system of claim 3, wherein the imager is at least a part of a smartphone.

12. The system of claim 3, wherein the space provides a size scale.

13. The system of claim 3, wherein the analyzing device performs chemical, biological and/or physical analysis of the microfiber.

14. The system of claim 3, wherein the analyzing device analyzes a protein, a nucleic acid, a small molecule, a cell, a bacterium, or a virus in or on the microfiber.

15. The system of claim 3, wherein the microfiber is a natural material, a synthetic material, or a naturally occurring material that is synthetically modified.

16. The system of claim 3, wherein the microfiber is selected from the group consisting of hair, a glass fiber, a glass microfiber, a cellulose fiber, a nitrocellulose fiber, a cellulose acetate fiber, a nylon fiber, a polyolefin fiber, a polyester fiber, a polycarbonate fiber, a polypropylene fiber, a polyvinylidene difluoride fiber, a polyethylene fiber, a polystyrene fiber, a polyurethane fiber, a polyphenylene oxide fiber, a poly(tetrafluoroethylene-co-hexafluoropropylene) fiber, a quartz fiber, a hydrophilic polymer/fiber, fiberglass, silk, spider silk, seed fiber, leaf fiber, bast fiber, fruit fiber, stalk fiber, animal fiber, collagen, keratin, fibroin, wool, cashmere, camel hair, avian fiber, chitin, chitosan, cotton, flax, hemp, jute, natural fiber composites, and any combination thereof.

17. The system of claim 3, wherein the microfiber is hair from a mammal.

18. The system of claim 3, wherein the microfiber is hair from a human.

19. The system of claim 3, wherein the analyzing device analyzes hair density, hair color, hair smoothness, hair texture, hair thickness, hair curliness, hair volume, or a combination of thereof.

20. The system of claim 3, wherein the analyzing device analyzes hair quality and determines a suitable hair care product for the subject.

21. The system of claim 3, wherein the analyzing device measures the pH value of the microfiber.

22. The system of claim 3, wherein the analyzing device provides a recommendation that is based on the analyzing.

23. The system of claim 3, wherein the analyzing device analyzes reactions of the microfiber with one or more chemical reagents.

24. The system of claim 3, wherein the analyzing device analyzes fluorescence imaging, bright field optical imaging, dark field optics, or spectrophotometric analysis.

25. The system of claim 3, wherein the analyzing device analyzes an immunoassay, a nucleic acid assay, a colorimetric assay, or an immunocytochemistry.

26. The system of claim 3, wherein the analyzing device determines hair volume that is related to the subject's health status, personal hygiene, dieting habits, and environmental conditions.

27. The system of claim 3, wherein the analyzing device analyzes hair quality and determines a suitable hair care product for the subject.

28. The device of claim 2, wherein the spacers are pillars.

29. The device of claim 1, wherein the groove depth is 500 µm or less.

30. The device of claim 1, wherein the groove depth is 100 µm or less.

31. The device of claim 1, wherein the groove cross-section is round, half-circle, ellipse, square, rectangle, triangle, polygon, ring-shaped, or any superposition thereof, or any shape that accommodates hair strand.

32. The device of claim 1, further comprising a hinge that connects the first plate and the second plate.

33. The device of claim 1, wherein the groove has a width of 2 mm or less.

34. The device of claim 1, wherein the groove runs across one edge of the surface of the plate to the opposite edge of the surface of the plate.

35. The device of claim 1, further comprising a plurality of grooves.

* * * * *